(12) United States Patent
Ametaj

US008920814B2

(10) Patent No.: US 8,920,814 B2
(45) Date of Patent: Dec. 30, 2014

(54) BACTERIAL ENDOTOXIN FOR THE PREVENTION OF METABOLIC DISORDERS AND BACTERIAL INFECTIONS

(75) Inventor: Burim N. Ametaj, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 676 days.

(21) Appl. No.: 12/529,445

(22) PCT Filed: Jun. 7, 2007

(86) PCT No.: PCT/CA2007/000995
§ 371 (c)(1),
(2), (4) Date: Dec. 7, 2009

(87) PCT Pub. No.: WO2008/106763
PCT Pub. Date: Sep. 12, 2008

(65) Prior Publication Data
US 2010/0113384 A1    May 6, 2010

Related U.S. Application Data

(60) Provisional application No. 60/893,709, filed on Mar. 8, 2007.

(51) Int. Cl.
| *A61K 39/02* | (2006.01) |
| *A23K 1/00* | (2006.01) |
| *A23K 1/18* | (2006.01) |
| *A61K 39/108* | (2006.01) |
| *A61K 31/739* | (2006.01) |
| *A23L 1/30* | (2006.01) |
| *A61K 39/00* | (2006.01) |

(52) U.S. Cl.
CPC ....... *A61K 39/0258* (2013.01); *A61K 2039/552* (2013.01); *A23K 1/008* (2013.01); *A61K 2039/55* (2013.01); *A23K 1/1813* (2013.01); *A61K 31/739* (2013.01); *A23L 1/30* (2013.01); *A61K 2039/542* (2013.01); *Y10S 424/823* (2013.01)
USPC .................. 424/236.1; 424/234.1; 424/241.1; 424/823

(58) Field of Classification Search
USPC .......................... 424/234.1, 236.1, 241.1, 823
See application file for complete search history.

(56) References Cited

U.S. PATENT DOCUMENTS

| 3,911,109 A | 10/1975 | Kenworthy et al. |
| 4,141,970 A | 2/1979 | Chidlow et al. |
| 2002/0051793 A1 | 5/2002 | Drabick |
| 2004/0147010 A1 | 7/2004 | Vidal et al. |
| 2004/0214794 A1 | 10/2004 | Grimmecke et al. |
| 2006/0153869 A1 | 7/2006 | MacAdam |

FOREIGN PATENT DOCUMENTS

| CA | 2044808 A1 | 12/1991 |
| EP | 0 405 315 B1 | 8/1995 |
| GB | 1 336 015 A | 7/1973 |
| WO | WO 02/16440 A2 | 2/2002 |

OTHER PUBLICATIONS

Abbas et al. Cellular and Molecular Immunology 4th edition chapter 15 p. 360-362, 2000.*
Ellis, R.W. (Chapter 29 of "Vaccines" [Plotkin, S.A. et al. (eds) published by W. B. Saunders company (Philadelphia) in 1988.*
Ametaj et al., "Strong relationships between mediators of the acute phase response and fatty liver in diary cows," Can. J. Anim. Sci., (2005), p. 165-175, vol. 85.
Austgen et al., "The Effects of Endotoxin on the Splanchnic Metabolism of Glutamine and Related Substrates," J. Trauma, (1991), p. 742-752, vol. 31.
Coppock et al., "Effect of Forage-Concentrate Ratio in Complete Feeds Fed ad Libitum on Feed Intake Prepartum and the Occurrence of Abomasal Displacement in Diary Cows", Journal of Dairy Science, (1972), p. 783-789, vol. 55.
Erb et al., "Path Model of Reproductive Disorders and Performance, Milk Fever, Mastitis, Milk Yield, and Culling in Holstein Cows," J. Dairy Sci., (1985), p. 3337-3349, vol. 68.
Goad et al., "Ruminal microbial and fermentative changes associated with experimentally induced subacute acidosis in steers," J. Anim. Sci., (1998), p. 234-241, vol. 76.
Goff, J.P., "Major Advances in Our Understanding of Nutritional Influences on Bovine Health," J. Dairy Sci., (2006), p. 1292-1301, vol. 89.
Gorg et al., "Lipopolysaccharide-induced Tyrosine Nitration and Inactivation of Hepatic Glutamine Synthetase in the Rat," Hepatology, (May 2005), p. 1065-1073, vol. 41.
Gozho et al., "Subacute Ruminal Acidosis Induces Ruminal Lipopolysaccharide Endotoxin Release and Triggers an Inflammatory Response," J. Dairy Sci., (2005), pp. 1399-1403, ISSN: 0022-0302, vol. 88.
Gozho et al., "Ruminal Lipopolysaccharide Concentration and Inflammatory Response During Grain-Induced Subacute Ruminal Acidosis in Dairy Cows," J. Dairy Sci., (Feb. 2007), pp. 856-866, ISSN: 0022-0302, vol. 90.
Grohn et al., "Epidemiology of Metabolic Disorders in Dairy Cattle: Association Among Host Characteristics, Disease, and Production", J. Diary Sci., (1989), p. 1876-1885, vol. 72.
Kleen et al., "Subacute Ruminal Acidosis (SARA): a Review", J. Vet. Med., (2003), p. 406-414, vol. 50.
Lobley, et al., "Glutamine in Animal Science and Production," J. Nutr., (2001), p. 2525S-2531S, vol. 131.
Meijer et al., "Glutamine Is a Potentially Limiting Amino Acid for Milk Production in Dairy Cows: A Hypothesis", Metabolism, (1993), p. 358-364, vol. 42.
Nagaraja et al., "Relationship of Rumen Gram-Negative Bacteria and Free Endotoxin to Lactic Acidosis in Cattle," J. Anim. Sci., (1978), p. 1329-1337, vol. 47.
Naylor J.M et al., "Relationships Between Metabolic Changes and Clinical Signs in Pregnant Sheep Given Endotoxin", Can. J. Vet. Res., (1986), pp. 402-409, ISSN: 0830-9000, vol. 50.

(Continued)

Primary Examiner — Jennifer Graser

(57) ABSTRACT

The invention provides compositions and methods for preventing a metabolic disorder or bacterial infection in a subject, the composition comprising a bacterial endotoxin.

13 Claims, 13 Drawing Sheets

(56) References Cited

OTHER PUBLICATIONS

Tomita et al., "Immunization of Dairy Cows with an *Escherichia coli* J5 Lipopolysaccharide Vaccine", *J. Dairy Sci.*, (1995), pp. 2178-2185, ISSN: 0022-0302, vol. 78.

Van Dorp et al., "An Epidemiologic Study of Disease in 32 Registered Holstein Dairy Herds in British Columbia", *Can. J. Vet. Res.*, (1999), p. 185-192, vol. 63.

Waldron et al., "Effect of Lipopolysaccharide on Indices of Peripheral and Hepatic Metabolism in Lactating Cows," *J. Dairy Sci.*, (2003), p. 3447-3459, vol. 86.

International Search Report mailed Dec. 10, 2007 in PCT/CA2007/000995 filed Jun. 7, 2007.

Written Opinion mailed Dec. 10, 2007 in PCT/CA2007/000995 filed Jun. 7, 2007.

International Search Report issued Jun. 5, 2012 in PCT/CA2012/050120.

Written Opinion of the International Searching Authority issued Jun. 5, 2012 in PCT/CA2012/050120.

Lehner et al., "Induction of Cross-Tolerance by Lipopolysaccharide and Highly Purified Lipoteichoic Acid Via Different Toll-Like Receptors Independent of Paracrine Mediators," The Journal of Immunology, vol. 166, pp. 5161-5167 (2001).

Kim et al., "Lipoteichoic Acid Isolated from *Lactobacillus plantarum* Inhibits Lipopolysaccharide-Induced TNF-α Production in THP-1 Cells and Endotoxin Shock in Mice," The Journal of Immunology, vol. 180, pp. 2553-2561 (2008).

Ametaj et al., "Repeated oral administration of lipopolysaccharide from *Escherichia coli* 0 I I I:B4 modulated humoral immune responses in periparturient dairy cows," Innate Immunity, vol. 18, No. 4, pp. 638-647 (2012).

Zebeli et al., "Intermittent parenteral administration of endoxtoxin triggers metabolic and immunological alterations typically associated with displaced abomasum and retained placenta in periparturient dairy cows," J. Dairy Sci., vol. 94, pp. 4968-4983 (2011).

\* cited by examiner

BACTERIAL ENDOTOXIN FOR THE PREVENTION OF METABOLIC DISORDERS AND BACTERIAL INFECTIONS

CROSS-REFERENCE TO RELATED APPLICATIONS

This application is a national stage of International PCT Application No. PCT/CA2007/000995, filed Jun. 7, 2007, and claims the benefit of U.S. Provisional Patent Application No. 60/893,709, filed Mar. 8, 2007, which is incorporated herein by reference.

FIELD OF THE INVENTION

The invention concerns the use of bacterial endotoxins for preventing metabolic disorders and bacterial infections.

BACKGROUND OF THE INVENTION

Metabolic disorders are diseases that involve changes in plasma metabolites of sick animals or humans. Almost 50% of dairy cows are affected by one or more metabolic diseases such as ketosis, fatty liver, laminitis, displaced abomasum, milk fever, downer cow syndrome, udder edema, metritis, retained placenta, infertility, or mastitis. The conventional view on metabolic disorders is that these diseases are related to the disturbance of one or more blood metabolites. These changes are generally interpreted as deficiencies or excesses of these nutrients in the diet, especially, around parturition.

High-grain diets (i.e. a diet rich in starch) may be implicated in the development of metabolic disorders. Feeding ruminant animals high-grain diets is a human-designed intervention to increase milk and meat production. However, ruminants do not naturally consume high-grain diets; rather, they eat mostly grass or forage diets. Since grain is rich in starch and poor in fiber content, feeding high-grain diets is associated with major changes in the gastrointestinal (GI) microflora, involving a switch from fiber-digesting bacteria to starch-digesting bacteria. Most of the starch-digesting bacteria are Gram-negative bacteria. These degrade starch to use it for their nutritional needs. During this process, large quantities of acids are released into the GI tract. As a result, the normally alkaline GI tract becomes more acidic. Furthermore, abundant starch increases the number of Gram-negative bacteria in the GI tract. This is associated with the release of great amounts (20-fold increase) of toxic compounds such as endotoxin or lipopolysaccharide (LPS). Endotoxin translocates into the host's blood circulation and causes a variety of alterations in blood metabolites, immunity, and health status.

Thus, metabolic disorders, particularly as a result of grain feeding in ruminant animals, are a significant problem and there remains a need for effective methods for preventing metabolic disorders, particularly in mammals such as dairy cattle.

SUMMARY OF THE INVENTION

The inventors have discovered that, surprisingly, administration of a bacterial endotoxin to a mammal is effective to prevent the development of metabolic disorders. It has further been discovered that the same approach is also effective for preventing bacterial infections.

Accordingly, in one aspect, the invention provides a composition for preventing a metabolic disorder or bacterial infection in a subject, said composition comprising a bacterial endotoxin.

In another aspect, the invention provides a method for preventing a metabolic disorder or bacterial infection in a subject, said method comprising administering to said mammal a composition comprising a bacterial endotoxin.

In another aspect, the invention provides use of a bacterial endotoxin for preventing a metabolic disorder or bacterial infection in a subject.

In another aspect, the invention provides use of a bacterial endotoxin in the preparation of a medicament for preventing a metabolic disorder or bacterial infection in a subject.

In another aspect, the invention provides a bacterial endotoxin for use in preventing a metabolic disorder or bacterial infection in a subject.

DETAILED DESCRIPTION

Figure 1:
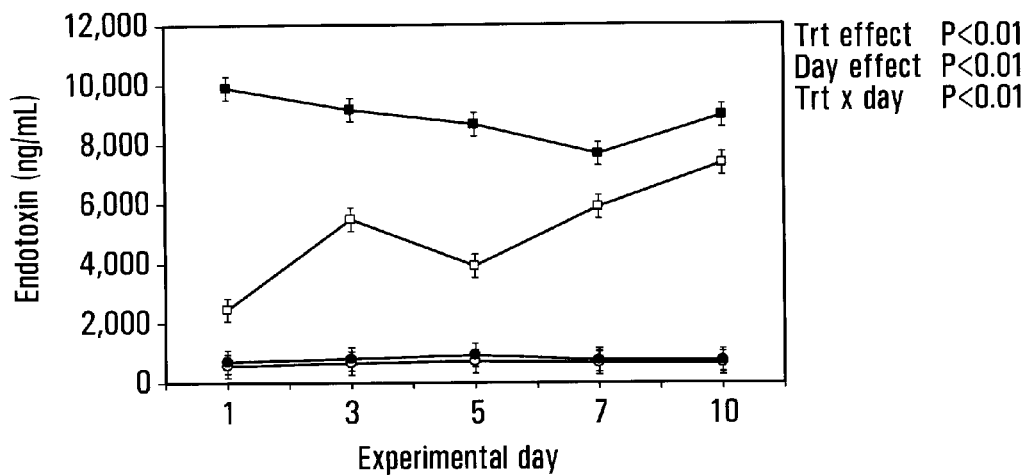
FIG. 1 is a graph depicting concentration of endotoxin (ng/mL) in the rumen fluid of early lactating (~60 DIM) cannulated Holstein dairy cows (n=8) fed 0% (○), 15% (●), 30% (□), or 45% (■) barley grain in a 4×4 Latin square design with 11-d of adaptation period and 10-d of measurements period.

Metabolic disorders are a group of diseases that affect dairy cows immediately after parturition. There are several metabolic disorders identified in dairy cows during the first month after parturition, the most significant of which are the following: (1) sub-acute and acute ruminal acidosis; (2) laminitis; (3) ketosis, (4) fatty liver, (5) left displaced abomasum (LDA), (6) milk fever; (7) downer cow; (8) retained placenta; (9) metritis, (10) mastitis, (11) udder edema; and (12) bloat. Dairy farmers lose approximately $142/cow per year for treatment of metabolic disorder in addition to milk loss in the first 30 days of lactation. More than half of dairy cows are affected by at least one metabolic disorder. This makes metabolic disorders of great economic importance.

The reason that these diseases are called metabolic disorders is related to the fact that they are associated with the disturbance of one or more blood metabolites in sick cows. For example, ketosis is associated with enhanced ketone bodies in the blood; fatty liver is associated with enhanced non-esterified fatty acids (NEFA) in the blood and their accumulation in the liver; acidosis is associated with increased production of volatile fatty acids (e.g., acetate, propionate, and butyrate) and organic acids (e.g., lactic acid) in the rumen and low rumen and blood pH; and milk fever is associated with decreased blood calcium. There is not yet a blood metabolite identified for some of the metabolic disorders such as downer cow, LDA, metritis, mastitis, or bloat. However, these diseases are associated with alteration of multiple blood metabolites.

The most interesting observation with regard to the occurrence of metabolic disorders is that they are highly associated with each other. For example, cows affected by milk fever are more prone to mastitis, retained placenta, metritis, LDA, dystocia, udder edema, and ketosis; cows affected by acidosis are more prone to laminitis, LDA, milk fever, mastitis, and fatty liver. Those affected by retained placenta are more prone to metritis, LDA, and ketosis. Ketosis and fatty liver are common findings in cows affected by milk fever, mastitis, laminitis, displaced abomasum, metritis, retained placenta and udder edema. Although these associations have been known for years by animal scientists, the reason behind these associations is not very well understood. One speculation is that there might be a common etiological factor that initiates the cascade of metabolic disorders. Therefore, scientists are searching to identify such a common causal agent of metabolic disorders; however, no such an agent has been identified so far.

Modern dairy cows have been selected by continuous genetic improvement and rigorous selection to achieve high milk production. Since high milk production cannot be maintained by forage alone, grain-based diets which are very rich in energy are fed to cows. The ruminal digestive system is not developed to digest high amounts of grain, and feeding grains which are rich in starch is associated with a decline in ruminal and colonic pH, change in osmotic pressure and shift in bacterial populations from cellulolytic to amylolytic bacteria. Most of the known starch digesters are Gram-negative bacteria and this shift in population is associated with a 20-fold increase in the amount of endotoxin in the ruminal fluid. Several epidemiological studies have shown that endotoxin from rumen Gram-negative bacteria has been implicated in diseases that are related to feeding high concentrate diets such as sudden death syndrome, ruminal acidosis, fatty liver, left displaced abomasum and laminitis. Ruminal epithelium lacks in mucus secretion and exposure to acidotic environment leads to inflammation and tissue degeneration. The acidotic environment, change in osmotic pressure and endotoxin may affect the permeability of the rumen and colon resulting in translocation of endotoxin in the circulation. Although the presence of endotoxin in the ruminal fluid has been documented, prior to the present invention there has been no convincing evidence of translocation into the circulation.

We hypothesized that the decline in the ruminal fluid and colon pH during conditions of sub-acute and acute acidosis together with the presence of endotoxin alter the permeability of these tissues and result in translocation of endotoxin into the systemic circulation.

Accordingly, we investigated whether common rumen fluid and colon concentrations of lipopolysaccharide (LPS) would affect the permeability of rumen and colon tissues to mannitol and LPS in Ussing chambers. In addition, this study was designed to answer the question whether acidic conditions similar to those found in the rumen fluid and colon during conditions of sub-acute and acute acidosis would affect the permeability of rumen and colon tissues to mannitol and LPS.

It was determined that permeability of rumen and colon tissues to mannitol were enhanced 6- and 5-fold by presence of E. coli LPS as well as acidic pH values (pH 4.5 and 5.5), respectively. The presence of endotoxin did not affect the permeability of rumen and colon tissues to mannitol at pH values ranging between 5.5 and 7.4. An individual variation in the permeability of rumen and colon tissues to mannitol was observed. The latter may explain the different responses and susceptibilities of ruminant animals to rumen acidosis.

Results of this study showed, for the first time, that conditions similar to sub-acute and acute acidosis that develop under feeding of high-grain diets as well as presence of LPS from E. coli strain B:055 increase several fold the permeability of rumen and colon tissues to mannitol. This indicates that rumen and colon tissues become leaky to toxic compounds under acidic conditions and presence of Gram-negative bacterial toxins.

Rumen pH values show that cows adjust within three days to feeding of barley grain at 0, 15, 30, and 45% of the diet on a DM-basis as well as 15% concentrate mix. However, rumen fluid pH values drop during the day at acidic values even after 10 days of feeding the grain mix. All diets containing more than 15% of barley grain reached acidic pH rumen values 8 h after feeding of the grain mix. Only the cows consuming the diet containing 0% barley grain maintained the rumen pH within normal ranges.

We then investigated how transition cows respond clinically to repeated oral and intravenous exposure to an E. coli antigen (E. coli lipopolysaccharide—("LPS")) during the 2 weeks before and 1 week after calving, and to determine the effects of repeated oral or intravenous administration of E. coli LPS on eating behaviour and milk yield during the transition period.

It was determined that both oral and intravenous administration of E. coli LPS increased the body temperature in cows before and after calving. Respiration rate differed with the route of antigen administration (i.e., oral increased and i/v decreased). No differences in rumen contractions and dry matter intake ("DMI") were identified amongst four treatment groups. Cows treated with E. coli LPS had slightly lower milk production than control cows.

The results of these experiments showed that toxic compounds released by Gram-negative bacteria including E. coli play an important role in clinical responses observed in cows around calving. Both oral and parenteral exposures to the E. coli LPS enhanced body temperature. The oral administration of the E. coli LPS induced respiration whereas parenteral administration lowered the respiration rate.

In a further study, the metabolic responses of dairy cows to repeated administration of an E. coli endotoxin around parturition was investigated. The results of this study showed that beta-hydroxybutyric acid ("BHBA") and non-esterified fatty acids ("NEFA") increased in all cows during the first week after calving. Cows treated orally with the E. coli LPS had lower concentrations of BHBA, NEFA, and cholesterol and higher concentrations of glucose in the plasma during the first week after parturition. Without intending to be bound by any particular theory, it is speculated that oral administration with the E. coli LPS has induced cows' mucosal immune responses against Gram-negative bacterial endotoxins and therefore has prevented the entrance of these toxins into the bloodstream.

Cows treated intravenously with E. coli LPS had higher concentrations of BHBA, NEFA, and cholesterol and decreased concentrations of glucose in plasma indicating a role for these toxins in the etiology and pathogenesis of ketosis and fatty liver. Control cows had higher plasma BHBA, NEFA, and cholesterol and lower plasma glucose.

Because oral administration of an E. coli LPS prevented postpartal enhancement of BHBA and NEFA, it suggests that toxins released in the rumen and translocated into the bloodstream play an important role in pathogenesis of ketosis and fatty liver in transition dairy cows and accordingly these results establish that vaccination with a bacterial endotoxin is useful in preventing metabolic disorders.

Translocation of endotoxin in the bloodstream is also known to cause damage to the gastrointestinal barrier. We have observed that low pH and presence of endotoxin makes rumen and colon tissues leaky. Therefore, vaccination with endotoxin may also be used to prevent infection from Gram-negative bacteria.

Endotoxin

Any bacterial endotoxin may be used in the practice of the invention. Endotoxins are cell-associated bacterial toxins. They generally compose part of the outer membrane of the cell wall of Gram-negative bacteria, whether pathogenic or not, such as *Escherichia coli, Salmonella, Shigella, Pseudomonas, Neisseria,* or *Haemophilus.* Many endotoxins are lipopolysaccharides (LPS), comprising a lipid component and a polysaccharide component. Toxicity of the endotoxin is associated with the lipid component (lipid A) and immunogenicity is associated with the polysaccharide component. Both lipid A and the polysaccharide components of LPS act as determinants of virulence in Gram-negative bacteria.

The structure of the lipid A component is highly conserved amongst Gram-negative bacteria. The polysaccharide component contains two regions. The first is known as the core (R) antigen or (R) polysaccharide. The core polysaccharide remains relatively constant within a bacterial genus but is structurally distinct amongst genera of bacteria. The second polysaccharide region is the somatic (O) antigen or (O) polysaccharide. The (O) polysaccharide varies substantially between species and even amongst strains of Gram-negative bacteria.

Endotoxins of the invention may be used in purified or unpurified form, provided that the endotoxin is not associated with components that interfere substantially with its utility.

In embodiments, purified endotoxins (for instance in crystalline form) may be used and are available from commercial sources such as Sigma-Aldrich. Synthetic endotoxins, such as synthetic LPS or LPS analogs may be used in practice of the invention. Truncated endotoxins, or portions or fractions of endotoxins comprising for example only the lipid A or core polysaccharide or (O) polysaccharide of LPS may be used as may be chimeric endotoxins comprising altered or heterologous lipid A or polysaccharide components.

Compositions

The endotoxin may be administered to the subject neat (i.e. without additional diluents, carriers, etc.) or in the form of, without limitation, a pharmaceutical composition comprising the endotoxin. The endotoxin may also be administered as a component of the subject's diet, e.g. mixed with the subject's food or water.

Pharmaceutical compositions may be for oral, nasal, rectal, intravaginal or other modes of administration. The composition comprises the endotoxin in combination with one or more physiologically acceptable ingredients, such as carriers, excipients and/or diluents. Compositions and formulations for oral administration are particularly preferred.

Pharmaceutical compositions may be prepared, for example, in unit dose forms, such as tablets, sachets, capsules, dragees, suppositories or ampoules. They may be prepared in a conventional manner, for example by means of conventional mixing, granulating, confectioning, dissolving or lyophilising processes.

Preferred are pharmaceutical compositions formulated for administration to the gastrointestinal tract, such as by oral or rectal administration. Oral administration is particularly preferred as a convenient and economical mode of administration. Pharmaceutical compositions of the present invention in the form of dosage units for oral administration may take the form of, for example, granules, tablets, capsules, liquids or dragees prepared together with physiologically acceptable carriers, excipients and/or diluents.

Typical physiologically acceptable ingredients include:
(a) binding agents such as starch (e.g. pregelatinised maize starch, wheat starch paste, rice starch paste, potato starch paste), polyvinylpyrrolidone, hydroxypropyl methylcellulose, gum tragacanth and/or gelatin;
(b) fillers such as sugars (e.g. lactose, saccharose, mannitol, sorbitol), amylopectin, cellulose preparations (e.g. microcrystalline cellulose), calcium phosphates (e.g. tricalcium phosphate, calcium hydrogen phosphatelactose) and/or titanium dioxide;
(c) lubricants such as stearic acid, calcium stearate, magnesium stearate, talc, silica, silicic acid, polyethylene glycol and/or waxes;
(d) disintegrants such as the above-mentioned starches, carboxymethyl starch, cross-linked polyvinylpyrrolidone, agar, alginic acid or a salt thereof (e.g. sodium alginate) and/or sodium starch glycollate;
(e) wetting agents such as sodium lauryl sulphate; and/or,
(f) stabilizers.

Soft gelatin capsules may be prepared with capsules containing a mixture of the bacterial endotoxin together with paraffin oil, liquid polyethylene glycols, vegetable oil, fat and/or another suitable vehicle for soft gelatin capsules. Plasticizers such as glycerol or sorbitol may also be used. Hard gelatin capsules may contain granules of the composition. Hard gelatin capsules may also contain the endotoxin in combination with solid powdered ingredients such as those listed above.

Liquid formulations for oral administration may be prepared in the form of solutions, syrups or suspensions. Liquid formulations typically comprise the bacterial endotoxin together with an excipient such as sugar or sugar alcohols, and a carrier such as ethanol, water, glycerol, propylene glycol, polyethylene glycol, almond oil, oily esters or mixtures thereof. If desired, such liquid formulations may also contain coloring agents, flavoring agents, saccharine, thickening agents (e.g. carboxymethyl cellulose), suspending agents (e.g. sorbitol syrup, methyl cellulose, hydrogenated edible fats), emulsifying agents (e.g. lecithin, acacia), and/or preservatives (e.g. methyl p-hydroxybenzoates, propyl p-hydroxybenzoates, sorbic acid). Liquid formulations for oral administration may also be prepared in the form of a dry powder to be reconstituted with water or another suitable vehicle prior to use.

In embodiments, the pharmaceutical compositions comprising endotoxin can be administered with a syringe.

The invention also provides kits or commercial packages comprising a composition as described above together with printed matter comprising instructions for using the composition for preventing a metabolic disorder or bacterial infection in a subject.

Dosage Regimens

The pharmaceutical composition will generally contain a therapeutically effective amount of the bacterial endotoxin, i.e. an amount that is effective, at dosages and for periods of time necessary, to achieve a desired prophylactic or therapeutic result, such as a reduction, inhibition, or prevention of disease onset or progression. A therapeutically effective amount may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects.

For any particular subject, specific dosage regimens may be adjusted over time according to the individual need and the professional judgement of the person administering or supervising the administration of the compositions.

In some embodiments wherein the subject is a pregnant animal such as a dairy cow, the composition may be administered to the subject from a time no more than four weeks prior to parturition to a time no more than four weeks after parturition. During this period the composition may preferably be administered about two times per week. For example, in embodiments, the composition may be administered two times per week for three weeks (e.g. two weeks before and one week after parturition), for a total of six administrations. The composition may be administered in a dose of from 0.01 to 1 μg endotoxin/kg body weight of the subject, more preferably from 0.01 to 0.1 μg endotoxin/kg body weight of the subject, or more particularly, at a dose of about 0.01, about 0.05, or about 0.1 μg endotoxin/kg body weight of the subject. In embodiments, the composition may be administered to the subject in a regimen comprising a series of increasing doses, for example where the dose is increased from about 0.01 to about 0.05 and further to about 0.1 μg endotoxin/body weight of the subject. In embodiments, then, the composition may be administered two times per week for three weeks (e.g. two weeks before and one week after parturition) in a regimen of increasing doses (e.g. wherein the dose is increased weekly) of for example about 0.01, about 0.05 and about 0.1 μg endotoxin/kg body weight of the subject.

Subjects

Compositions of the invention may be used in prevention of metabolic disorders in a wide range of subjects including mammals and birds, including, without limitation: humans; livestock such as cattle, horses, goats, sheep, and pigs; companion animals such as dogs and cats; rabbits and domesticated fowl such as chickens, ducks and geese.

In one embodiment, the subject is a ruminant mammal, such as, without limitation, a cow, goat, sheep, llama, bison or deer. In an embodiment, the subject is a pregnant or has recently given birth, such as a ruminant mammal within about 4 weeks before or after parturition.

Disorders

The compositions of the invention are useful for preventing metabolic disorders and bacterial infections. As used herein, the term "preventing" includes, without limitation, preventing, reducing, or delaying the onset of at least one symptom of a metabolic disorder of interest. In an embodiment, a metabolic disorder may be caused by or associated with parturition in the subject and/or the feeding of a diet containing an elevated proportion of grain-based feed or easily digestible carbohydrates. The metabolic disorder may be associated with or caused by increased permeability of the colon or rumen, particularly increased permeability that permits bacterial endotoxins to escape the rumen or colon and infiltrate the bloodstream. Metabolic disorders that may be prevented in animals, particularly ruminant mammals include without limitation ruminal acidosis, laminitis, ketosis, fatty liver, left displaced abomasum, milk fever, downer cow, retained placenta, metritis, mastitis, udder edema or bloat. Metabolic disorders that may be prevented in humans include, without limitation abdominal obesity, impaired glucose regulation, raised triglycerides, decreased high-density lipoprotein cholesterol, elevated blood pressure, hyperinsulinemia with underlying insulin resistance, atherosclerosis, cardiovascular disease or rheumatic inflammatory disease.

Bacterial infections that may be prevented include, without limitation, bacterial infections caused by endotoxin-producing Gram-negative bacteria, including, without limitation *Escherichia coli, Salmonella, Shigella, Pseudomonas, Neisseria,* or *Haemophilus.*

The invention is further illustrated by the following non-limiting examples.

Example 1

In an experiment conducted at Dairy Research and Technology Centre (DRTC; University of Alberta) eight cannulated Holstein dairy cows (~60 DIM) were divided into 4 groups of 2 cows each and were fed 4 different diets containing 0, 15, 30, and 45% barley grain as well as 15% concentrate mix (DM basis) in a 4×4 Latin square design with 4 periods of 21 d each (11-d of adaptation and 10-d of measurements period).

This experiment provided evidence that concentration of ruminal endotoxin is increased in dairy cows fed increasing proportions of barley grain.

Data on FIG. 1 indicate that concentration of endotoxin (or lipopolysaccharide) in the rumen fluid of cows fed 30 and 45% barley grain (DM basis) in the diet was 8- to 14-fold higher than cows fed no barley grain (0% on a DM basis) and 6- to 11-fold higher than cows fed 15% barley grain, respectively. Cows were fed the diets for the first 11-d of adaptation period and then for another 10-d during the measurement period. Rumen and blood samples were collected during day 1, 3, 5, 7, and 10 of measurements (or experimental) period. Results were processed statistically and they indicate a treatment effect, a day effect as well as a day x treatment effect.

This experiment also provided evidence that increased concentration of ruminal endotoxin stimulates an inflammatory response in transition dairy cows.

Figure 2:
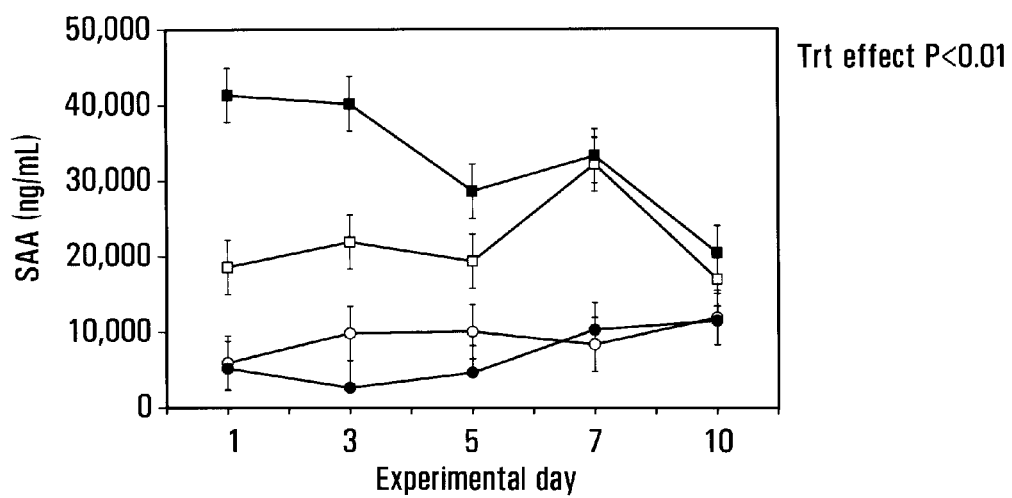
FIG. 2 is a graph depicting concentration of serum amyloid A (SAA) in the plasma (ng/mL) of early lactating (~60 DIM) cannulated Holstein dairy cows (n=8) fed 0% (○), 15% (●), 30% (□), or 45% (■) barley grain in a 4×4 Latin square design with 11-d of adaptation period and 10-d of measurement period.
Figure 3:
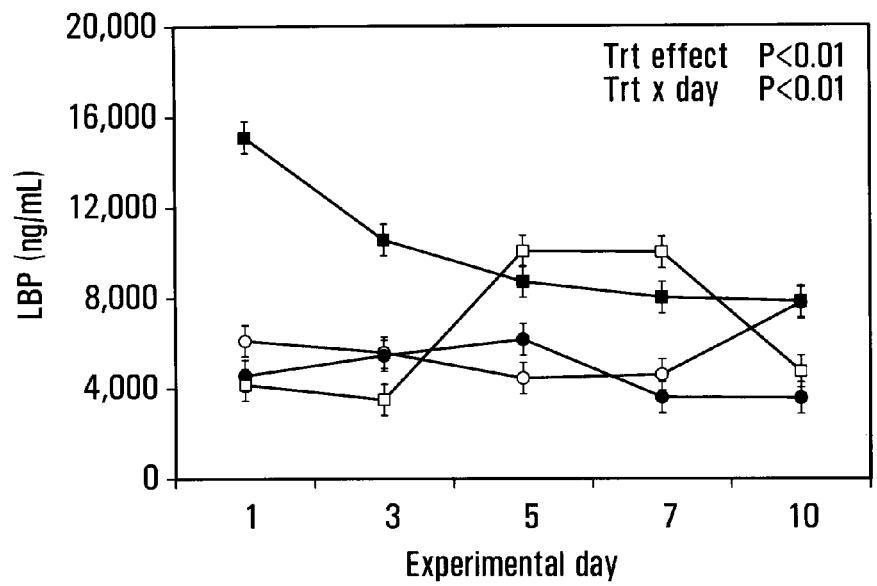
FIG. 3 is a graph depicting concentration of lipopolysaccharide binding protein (LBP) in the plasma (ng/mL) of early lactating (~60 DIM) cannulated Holstein dairy cows (n=8) fed 0% (○), 15% (●), 30% (□), or 45% (■) barley grain in a 4×4 Latin square design with 11-d of adaptation period and 10-d of measurement period.
Figure 4:
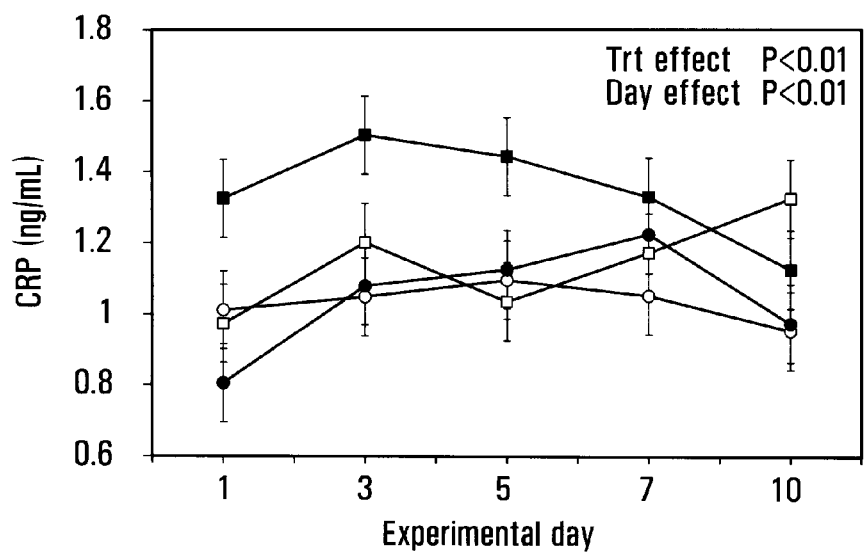
FIG. 4 is a graph depicting concentration of C-reactive protein (ng/mL) in the plasma of early lactating (~60 DIM) cannulated Holstein dairy cows (n=8) fed 0% (○), 15% (●), 30% (□), or 45% (■) barley grain in a 4×4 Latin square design with 11-d of adaptation period and 10-d of measurement period.

FIGS. 2, 3, and 4 show that cows fed higher proportions of barley grain (30 and 45%) had higher plasma concentrations of serum amyloid A (SAA), lipopolysaccharide-binding protein (LBP), and C-reactive protein (CRP) in the plasma compared to cows receiving lower proportions of barley grain (0 or 15%). Enhanced plasma concentrations of these three acute phase proteins indicate translocation of endotoxin into the blood circulation. The three acute phase proteins deal mainly with binding, neutralization, and removal of endotoxin from circulation as well as with activation of cell-mediated immunity (i.e., macrophages). In conclusion, these data show that endotoxin is translocated into the bloodstream of dairy cows fed high proportions of barley grain and induces an acute phase response reflected by several fold increases in the plasma concentration of SAA, LBP, and CRP.

Another in vitro experiment further provided evidence that acidic pH and presence of endotoxin makes rumen and colon tissues leaky to endotoxin and other non-nutritious compounds.

Figure 5:
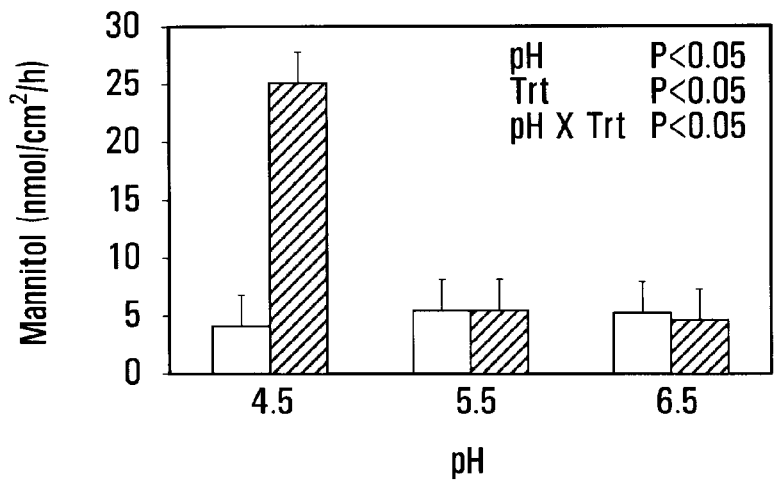
FIG. 5 is a graph depicting permeability of rumen tissue (obtained from killed feedlot steers) to $^3$H-labeled mannitol under different pH values and in the presence (■) or absence (□) of lipopolysaccharide (LPS) from $E.\ coli$ B:055 in an Ussing chamber.
Figure 6:
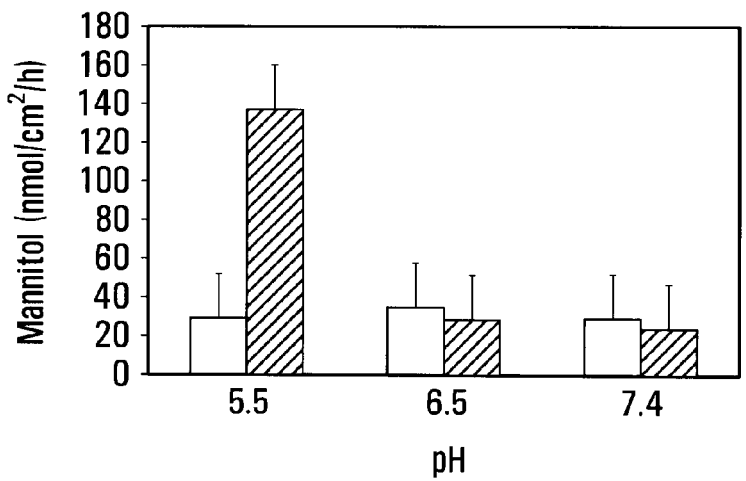
FIG. 6 is a graph depicting permeability of colon tissue (obtained from killed feedlot steers) to $^3$H-labeled mannitol under different pH values and in the presence (■) or absence (□) of lipopolysaccharide (LPS) from $E.\ coli$ B:055 in an Ussing chamber.

FIGS. 5 and 6 show that during acidic pH (pH 4.5 for the rumen tissue and pH 5.5 for colon tissue) similar with ruminal and colon pH values during acute ruminal acidosis and presence of lipopolysaccharide (LPS) from *Escherichia coli* 0:B55 (at a concentration of 500 μg/mL) permeability of rumen and colon tissues to $^3$H-mannitol increased 4- and 5-fold, respectively. Mannitol is a monosaccharide with a molecular weight of 182 daltons and normally is not metabolized by mammalian tissues. Mannitol normally goes through mucosal tissues in small amounts and has been used to evaluate the integrity of mucosal barriers. Enhanced permeability of rumen and colon tissues to mannitol indicates that rumen and colon tissues are damaged compared to controls. Both acidic pH and presence of LPS disrupts mucosal membranes and make them leaky to bacteria and toxic compounds like endotoxin.

Figure 7:
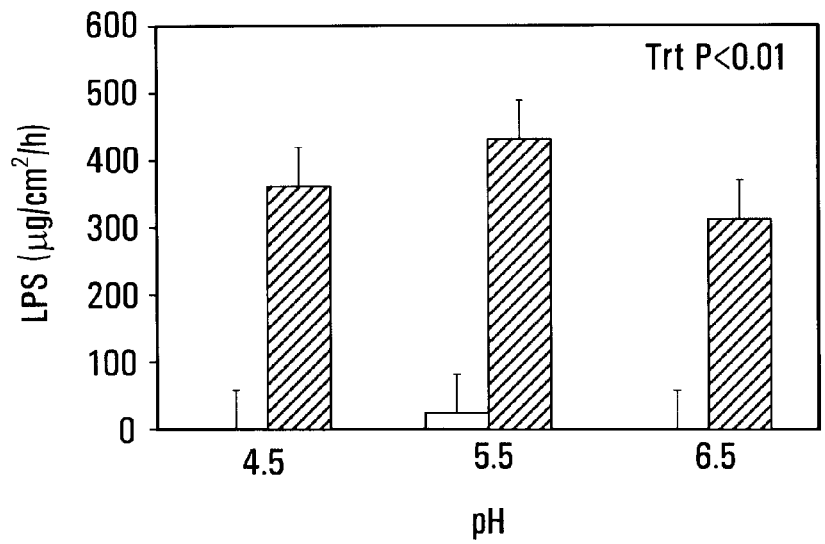
FIG. 7 is a graph depicting translocation of LPS across rumen tissue (obtained from killed feedlot steers) under different pH values and in the presence (■) or absence (□) of lipopolysaccharide (LPS) from $E.\ coli$ B:055 in an Ussing chamber.
Figure 8:
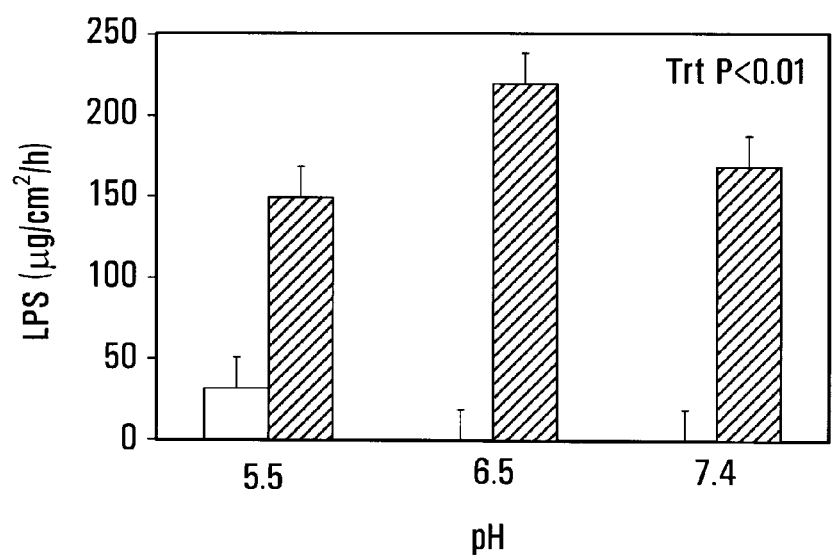
FIG. 8 is a graph depicting translocation of LPS across colon tissue (obtained from killed feedlot steers) under different pH values and in the presence (■) or absence (□) of lipopolysaccharide (LPS) from $E.\ coli$ B:055 in an Ussing chamber.

On the other hand, FIGS. 7 and 8 show that permeability of rumen and colon tissues to LPS were not affected by the pH value. This means that LPS went through the mucosal membranes (rumen and colon tissues) independently of the pH value. This suggests that when there is free endotoxin (i.e., LPS) in the rumen or colon fluid it translocates into the bloodstream of the host.

Example 2

This example demonstrates that oral vaccination against lipopolysaccharide from *Escherichia coli* 0111:B4 protects cows from postpartal metabolic disorders.

Animals and Treatments

During their final 3 wk prepartum, 32 multiparous Holstein cows were housed in a tie-stall barn with wood shavings for bedding, the number at any given time varied depending on the number of cows at that stage of gestation. Cows were blocked based on their parity, previous milk production as well as their expected day of calving and randomly assigned to one of the four treatment groups (8 cows/group) in a randomized blocked design 2 wk before the expected day of calving until 4 wk postpartum. Cows were offered dry-period and early-lactation diets, formulated according to NRC recommendation (2001) for transition dairy cows. The ingredient and nutrient composition of the dry-period- and early-lactation-diets are shown in Table 1.

TABLE 1

Diet composition and nutrients supplied by prepartum and postpartum diets[1] (% DM basis).

| Item | Prepartum | Postpartum |
| --- | --- | --- |
| Barley steam roll, | 16.41 | 29.78 |
| Corn steam roll, | 4.00 | 7.94 |
| Grass hay | 10.00 | — |
| Alfalfa hay late veg, | — | 9.61 |
| Alfalfa silage early, | — | 19.86 |
| Barley silage, | 60.23 | 20.31 |
| Dairy supplement[1] | 1.09 | 12.50 |
| Animate[2] | 4.84 | — |
| Molasses, beet sugar, | 0.55 | — |
| Vehgetable oil, | 0.70 | — |
| Limestone, | 1.56 | — |
| Vitamin E[3] | 0.39 | — |
| Vitamin $D_3$[4] | 0.23 | — |
| Energy and nutrient: | | |
| DM, | 43.67 | 54.04 |
| $NE_1$,[5] Mcal/kg, | 1.55 | 1.71 |
| NDF, | 45.31 | 27.82 |
| ADF, | 26.70 | 15.71 |
| NFC,[6] | 30.30 | 42.19 |
| Crude fat, | 3.70 | 4.61 |
| CP, | 14.71 | 18.13 |
| Ca, | 0.94 | 1.11 |
| P, | 0.40 | 0.50 |
| K, | 1.88 | 1.48 |
| Mg, | 0.40 | 0.39 |

[1]Supplied by Champion Feed Services Ltd. Barrhead, AB, Canada, contained malt sprouts (0.1%), canola fines (12.47%), canola meal (6.0%), corn gluten (25.0%), fish herring meal (10.0%), peas ground (4.0%), soy bean meal (10.0%), canola oil/soya oil (3.0%), canola oil (3.0%), megalac (7.5%), calcium carbonate (1.5%), maglox 58% (1.6%), Dicalcium phosphate(5.2%), Salt potash (3.1%), sodium bicarbonate (5.0%), vitamin E 500 (0.03%), and CFS dairy premix (1.6%).
[2]Anionic mineral supplemented for non lactating dairy cows, contained crude protein (Min, 35.0%), equivalent crude protein from non protein sources (Max, 25%), calcium (actual, 1.10%), magnesium (actual, 3.65), sulfure (actual, 4.65%), chlorine (actual, 11.90%), and (Na + K) − (Cl + S), (actual, −6047 meq/kg).
[3]Contained 5000 IU/kg.
[4]Contained 500,000 IU/kg.
[5]Based on weighted averages values provided by Champion Feed Services Ltd. and calculated according to NRC (2001).
[6]NFC was calculated as: 100 − [(NDF − NDFCP) + CP + ether extract + Ash] (NRC, 2001).

Diets were mixed and offered as TMR individually once a day at 0600 h. Orts were recorded and discarded before the next feeding each day and the amount of feed was adjusted to ensure a 10% feed residual. Cows were milked twice a day at 0400 and 1500 h, and milk yield was recorded electronically every day for the first 28 days of lactation. All clinical disease and medication were recorded daily during the whole experimental period. The experiment was conducted at the University of Alberta Dairy Research and Technology Center, Edmonton, Canada. All cows were managed and treated in accordance with the guidelines established by the Canadian Council on Animal Care (1993) and all animal-related procedures were approved by the University of Alberta Faculty Animal Policy and Welfare Committee.

The four groups of cows were administered on d 14, 11, 7, and 4 before the expected day of parturition as well as on d 1 and 3 after parturition, one of the following treatments: (1) oral delivery of 2 mL of saline (0.15 M NaCl), (2) oral delivery of 2 mL of saline containing lipopolysaccharide (LPS) from *Escherichia coli* 0111:B4 (Sigma, St. Louis, Mo.), (3) intravenous delivery of 100 mL of saline (0.15 M NaCl), or (4) intravenous delivery of 100 mL of saline containing LPS from *E. coli* 0111:B4. A 5 mL syringe was used for administration of treatment into the oral cavity. The amount of LPS given to cows orally or intravenously (iv) was as follows: (1) on d 14 and 11 before the expected day of parturition 0.01 µg/kg of BW dissolved in 2 mL (oral) or 100 mL (iv) of saline, (2) on d 7 and 4 before the expected day of parturition 0.05 µg/kg of BW dissolved in 2 mL (oral) or 100 mL (iv) of saline, and (3) on d 1 and 3 after parturition 0.1 µg/kg of BW dissolved in 2 mL (oral) or 100 mL (iv) of saline. Cows were given one flat dose of LPS based on the 650 kg average body weight of cows at Dairy Research and Technology Transfer. Rectal temperature, respiration rate, and rumen contraction was measured from all cows 15 min before as well as 60, 120, 180, 240, 300, and 360 min after administration of treatment.

Blood Sampling and Laboratory Analyses

A catheter was introduced into the jugular vein 1 h before the administration of treatment to all cows in the experiment. Blood samples were obtained from the jugular catheter 15 min before as well as at 15, 30, 60, 120, 180, 240, 300, and 360 min after administration of treatment on d 14, 11, 7, and 4 before the expected day of parturition as well as on d 1 and 3 after parturition. Also, 1 single blood sample was obtained during d 10, 17, and 24 after parturition.

Blood was collected into 10-ml Vacutainer tubes (Beckton Dickinson and Co., Rutherford, N.J.) containing $K_3$-EDTA, and plasma was prepared by centrifugation within 20 min. Plasma samples were stored at $-20°$ C. until analyzed for concentrations of serum amyloid A (SAA), lipopolysaccharide-binding protein (LBP), haptoglobin, C-reactive protein (CRP), glucose, insulin, non-esterified fatty acids (NEFA), beta-hydroxybutyric acid (BHBA), lactate, cholesterol, cortisol, calcium, copper, iron, zinc as well as anti-LPS immunoglobulin A, G, and M.

Evidence that Vaccination of Transition Cows Against Endotoxin Prevents Occurrence of Metabolic Disorders in Dairy Cows Immediately after Parturition:

The clinical data presented below demonstrate that cows vaccinated against LPS (oral LPS group) were not affected by any metabolic disorders during the first 30 days after parturition. There was only one cow (i.e., 12% of the whole group) affected by lameness and mastitis more than 30 days after parturition. On the other hand, 7 out of 9 cows (or 78% of the group) from the control group (oral saline group) were affected by one or multiple metabolic disorders. One cow from the saline-treated group had a dead calf. Another cow from the control group became a downer cow and she was killed because she could not stand on her feet. That cow was substituted by a new cow to have 8 cows per group. In conclusion, the clinical data indicate that the vaccine reduced by 100% the incidence of metabolic disorders within the first 30 d after parturition and by 66% after 30 d of parturition.

Oral Saline
Cow 2360—Off feed five days after calving, Temp=40 c.
Cow 2113—Calf born dead, Retained placenta, metritis.
Cow 2013—Calved on day 1 exhibiting Mastitis, off feed, Temp 39.1 cc, Mastitis on day 49.
Cow 2163—Calved day 1. Off feed day 21, Fatty liver on day 29.
Cow 2412—Calved day 1, Ketosis day 4.
Cow 2168—Normal
Cow 2268—Normal
Cow 2371—Calved day 1, Off feed, Antibiotics administered.
Cow 307—Died due to fatty liver and downer cow syndrome.

Figure 9:
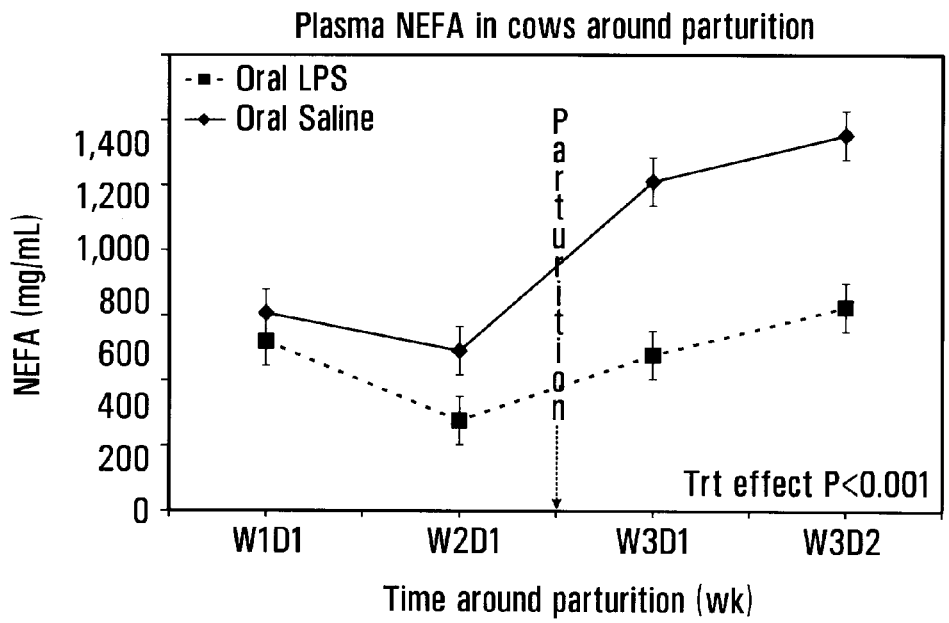
FIG. 9 is a graph depicting concentration of non-esterified fatty acid (NEFA; mg/mL) in the plasma of dairy cows treated with: 1) oral LPS from $E.\ coli$ 0111:B4 (- -■- -), or 2) oral saline (--◆--) around parturition (W1D1=week 1 day 1 of vaccination; W2D1=week 2 day 1 of vaccination; W3D1=week 3 day 1 of vaccination; and W3D2=week 3 day 2 of vaccination).
Figure 10:
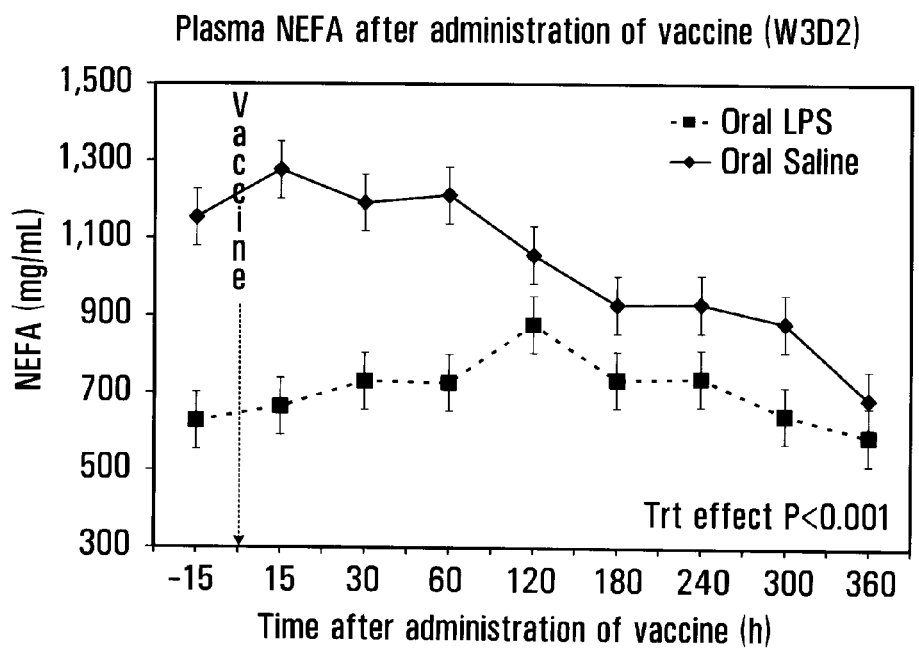
FIG. 10 is a graph depicting concentration of non-esterified fatty acids (NEFA; mg/mL) in the plasma of dairy cows treated with: 1) oral LPS from *E. coli* 0111:B4 (- -♦- -), or 2) oral saline (--♦--) on the first wk after parturition (W3D2=week 3 day 2 of vaccination) before and after vaccination.
Figure 11:
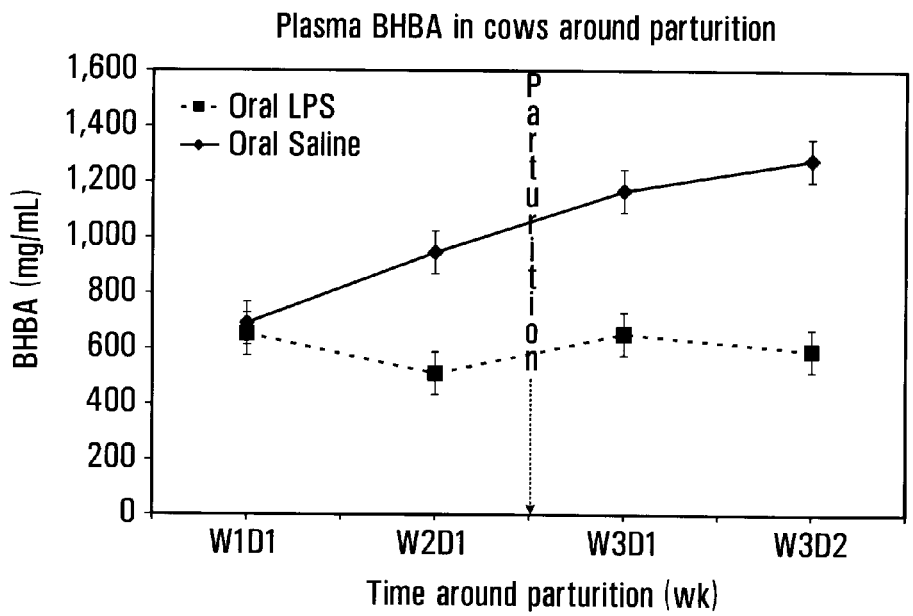
FIG. 11 is a graph depicting concentration of β-hydroxy butyric acid (BHBA; mg/mL) in the plasma of dairy cows treated with: 1) oral LPS from *E. coli* 0111:84 (- -■- -), or 2) oral saline (-♦-) around parturition (W1D1=week 1 day 1 of vaccination; W2D1=week 2 day 1 of vaccination; W3D1=week 3 day 1 of vaccination; and W3D2=week 3 day 2 of vaccination).
Figure 12:
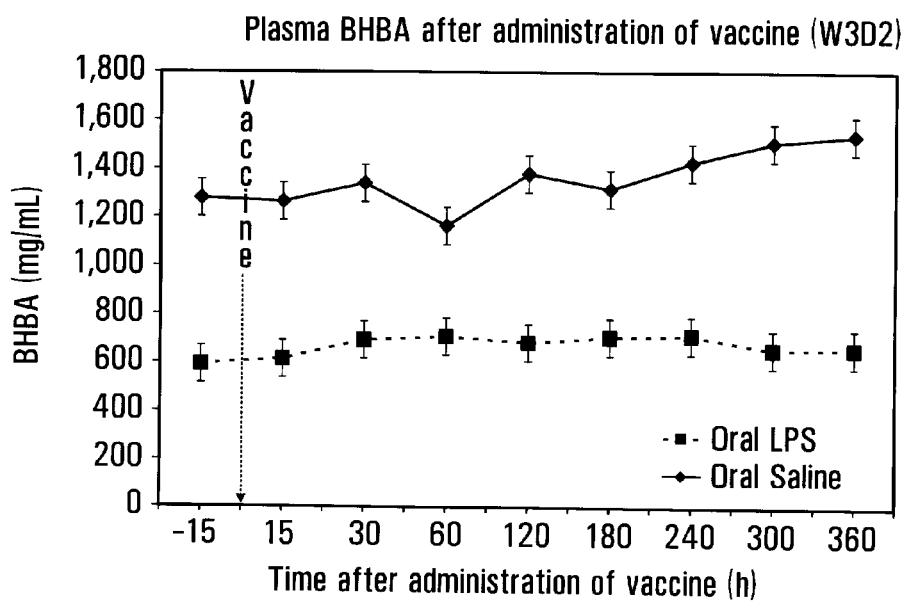
FIG. 12 is a graph depicting concentration of β-hydroxy butyric acid (BHBA; mg/mL) in the plasma of dairy cows treated with: 1) oral LPS from *E. coli* 0111:B4 (- -■- -), or 2) oral saline (-♦-) on the first wk after parturition (W3D2=week 3 day 2 of vaccination) before and after vaccination.

Oral LPS
Cow 2349—Normal
Cow 2369—Normal
Cow 2370—Normal—Calved day 1, Lameness day 44, Mastitis day 71
Cow 2310—Normal
Cow 2406—Normal
Cow 2417—Normal
Cow 2277—Normal
Cow 2423—Normal Evidence that Oral Vaccination Against Endotoxin is Associated with Improved Immune Responses and Metabolic Status of the Transition Cows FIGS. 9, 10, 11, and 12 show that vaccination against LPS prevented postpartal increase of plasma non-esterified fatty acids (NEFA) and beta-hydroxybutyric acid (BHBA) in cows after parturition. It is an established fact that plasma NEFA and BHBA increase in cows immediately after parturition. High concentrations of NEFA are strongly associated with fatty liver, a disease that affects 50% of dairy cows in a herd and is associated with 25% death rate if cows are not treated. Also, high plasma BHBA is highly associated with ketosis, a metabolic disorder that affects 30% of dairy cows in a herd. FIGS. 9 and 11 show that both plasma NEFA and BHBA did not change during the transition period and were lower in vaccinated cows compared to control cows. In addition, FIGS. 10 and 12 show that plasma NEFA and BHBA are lower in vaccinated cows during 6 h after administration of the vaccine or saline on the first week after parturition (W3D3=day 3 of week 3 after initiation of vaccination).

Figure 13:
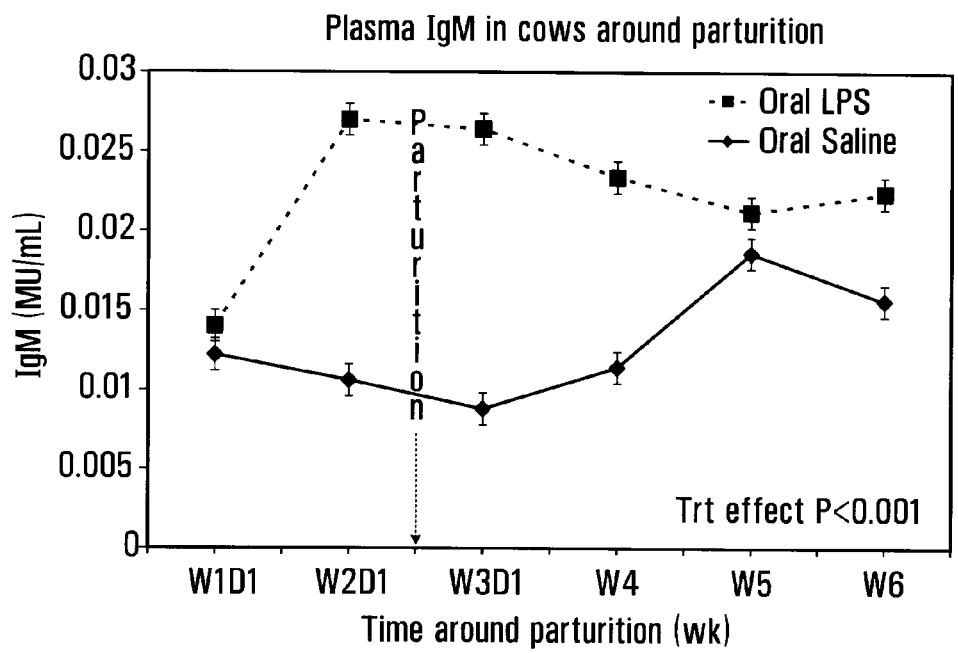
FIG. 13 is a graph depicting concentration of immunoglobulin M (IgM; MU/mL) in the plasma of dairy cows treated with: 1) oral LPS from *E. coli* 0111:B4 (- -■- -), 2) oral saline (-♦-), around parturition (W1D1=week 1 day 1 of vaccination; W2D1=week 2 day 1 of vaccination; W3D1=week 3 day 1 of vaccination; and W3D2=week 3 day 2 of vaccination; and W4, 5, and 6=week 4, 5, and 6 of the experiment).
Figure 14:
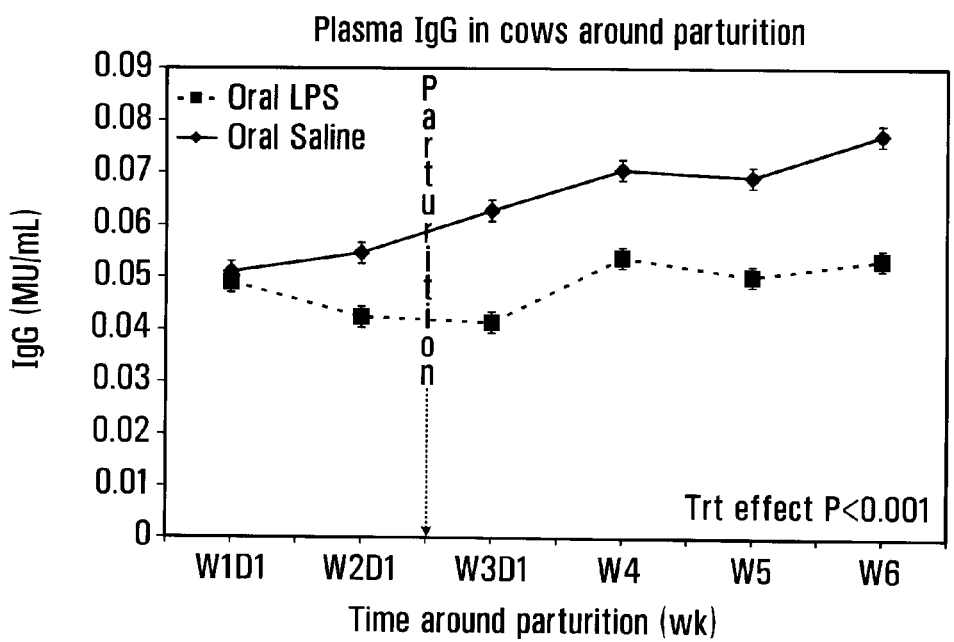
FIG. 14 is a graph depicting concentration of immunoglobulin G (IgG; MU/mL) in plasma of dairy cows treated with: 1) oral LPS from *E. coli* 0111:B4 (- -■- -), 2) oral saline (-♦-) around parturition (W1D1=week 1 day 1 of vaccination; W2D1=week 2 day 1; W3D1=week 3 day 1; and W3D2=week 3 day 2 of vaccination; and W4, 5, and 6=week 4, 5, and 6 of the experiment).
Figure 15:
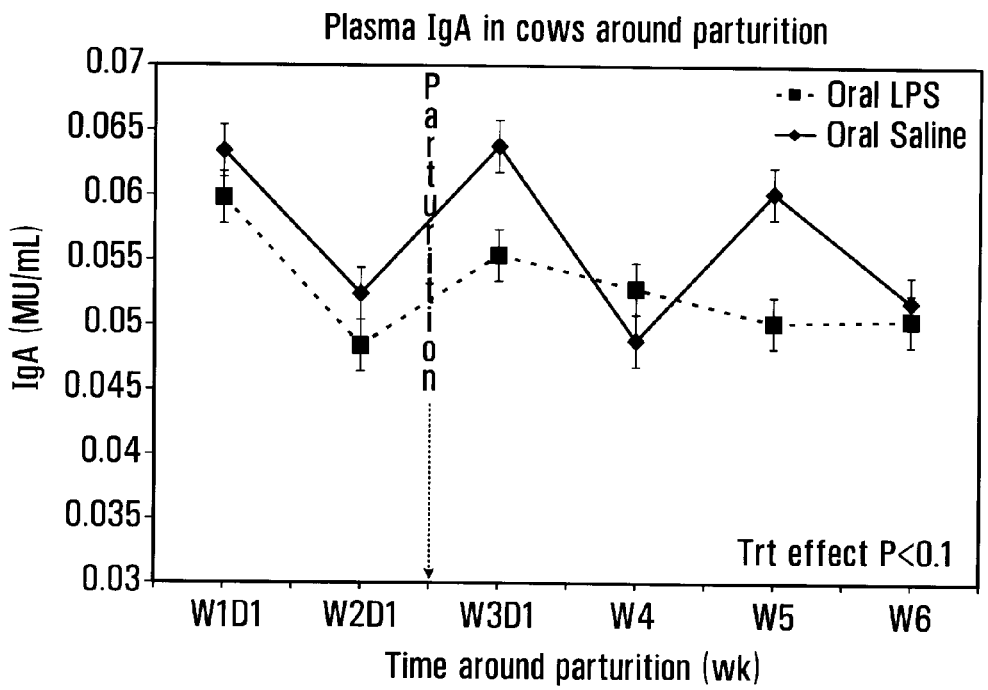
FIG. 15 is a graph depicting concentration of immunoglobulin A (IgA; MU/mL) in plasma of dairy cows treated with: 1) oral LPS from *E. coli* 0111:B4 (- -■- -), 2) oral saline (-♦-) around parturition (W1D1=week 1 day 1 of vaccination; W2D1=week 2 day 1 of vaccination; W3D1=week 3 day 1 of vaccination; and W3D2=week 3 day 2 of vaccination; and W4, 5, and 6=week 4, 5, and 6 of the experiment).

FIGS. 13, 14, and 15 show plasma concentrations of immunoglobulin M, G, and A in both groups of cows. Results show that vaccination increased plasma concentration of immunoglobulin M (IgM) several fold in vaccinated cows. These antibodies are specific anti-LPS antibodies, known also as Endocab or endotoxin antibodies. Presence of J chain in IgM antibodies allows them to be secreted in the mucosal surfaces. Although IgA is the major immunoglobulin found in mucosal secretions, IgM plays an important accessory role as a secretory immunoglobulin. Also, specific plasma anti-endotoxin IgG antibodies were lower in vaccinated cows compared to control cows indicating no entrance of endotoxin in the blood circulation of the vaccinated cows. Finally, plasma IgA antibodies against endotoxin were lower in vaccinated cows compared with the control ones, although the difference did not reach significant level. This shows again that the amount of endotoxin entered in circulation is lower in vaccinated cows. In addition, it suggests that IgA is secreted in the mucosal surfaces (i.e., gastro-intestinal tract to protect cows from translocation of endotoxin into blood circulation).

Figure 16:
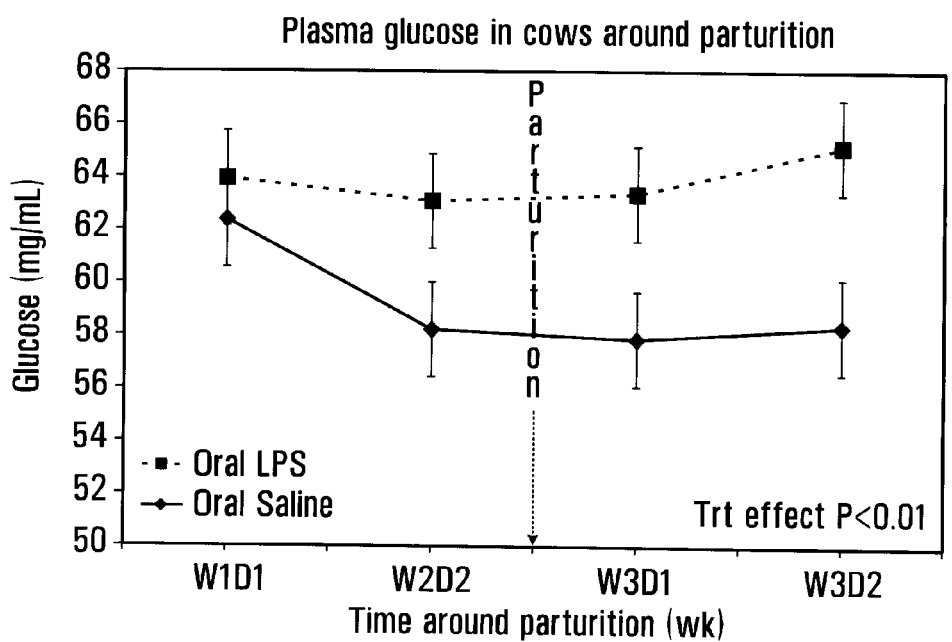
FIG. 16 is a graph depicting concentration of glucose (mg/mL) in the plasma of dairy cows treated with: 1) oral LPS from *E. coli* 0111:B4 (-- ■- - ), 2) oral saline (-♦-) around parturition (W1D2 week 1 day 1 of vaccination; W2D1=week 2 day 1 of vaccination; W3D1 week 3 day 1 of vaccination; and W3D2 week 3 day 2 of vaccination)
Figure 17:
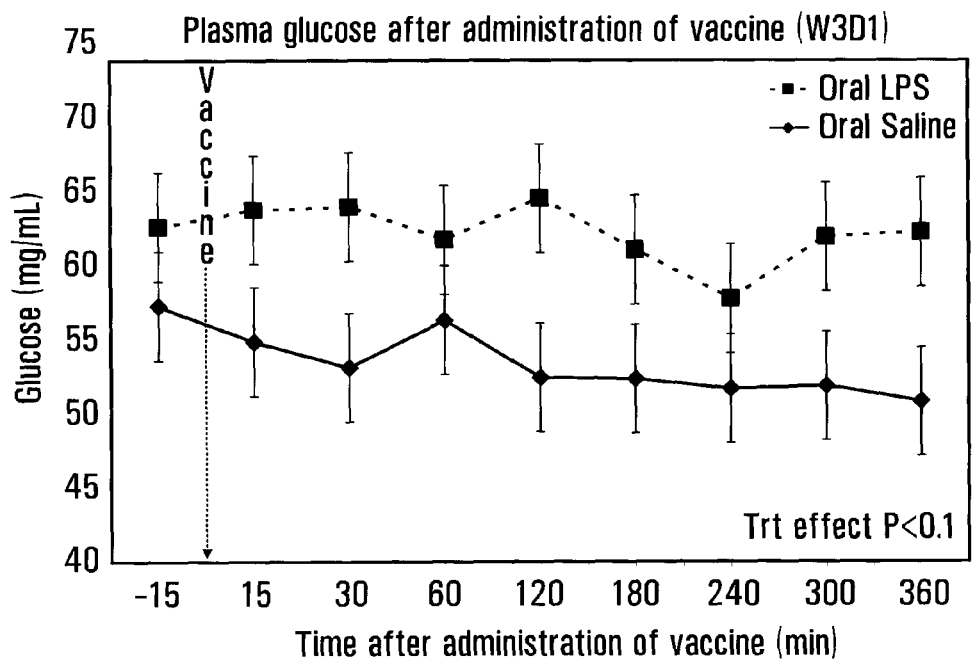
FIG. 17 is a graph depicting concentration of glucose (mg/mL) in the plasma of dairy cows treated with: 1) oral LPS from *E. coli* 0111:B4 (- -■- -), or 2) oral saline (-♦-) on the first wk after parturition (W3D1=week 3 day 1 of vaccination) before and after vaccination.
Figure 18:
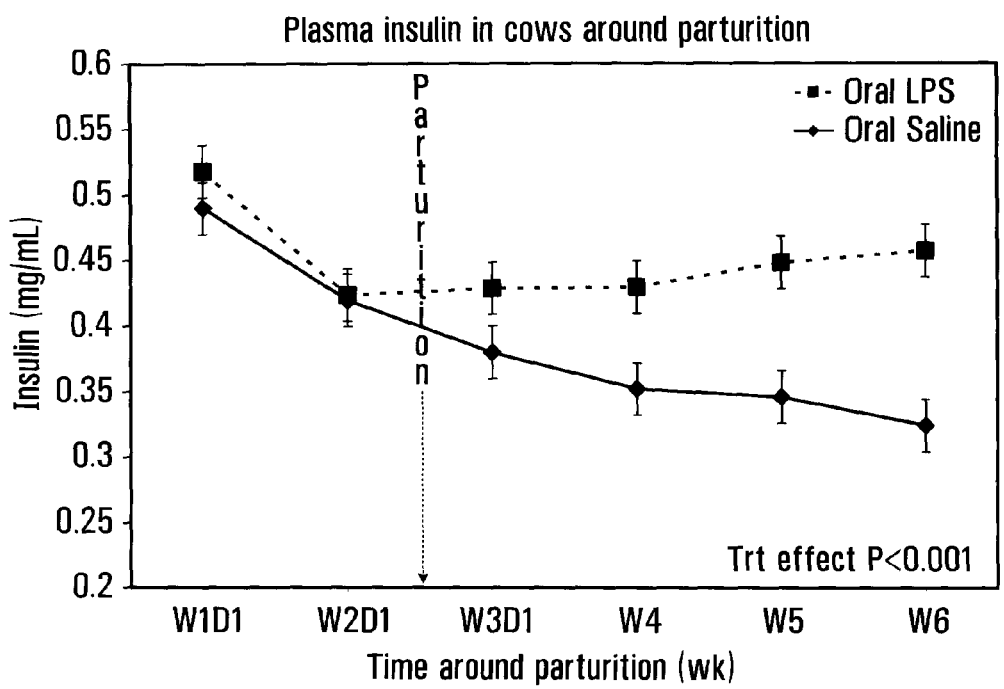
FIG. 18 is a graph depicting concentration of insulin (mg/mL) in plasma of dairy cows treated with: 1) oral LPS from *E. coli* 0111:B4 (- -■- -), or 2) oral saline (--♦--) around parturition (W1D1, or 2=week 1 day 1 or day 2 of vaccination; W2D1, or 2=week 2 day 1 or day 2 of vaccination; W3D1, or 2=week 3 day 1 or day 2 of vaccination; and W4, 5, or 6=week 4, 5, or 6 of the experiment).

FIGS. 16, 17, and 18 show plasma concentrations of glucose and insulin in both vaccinated and control cows. As shown in FIG. 16, concentration of glucose in plasma did not change and were higher in vaccinated cows during the 2 wk before and 1 wk after calving. However, plasma glucose decreased in control cows right before calving and stayed low during the week after calving. Moreover, FIG. 17 shows higher plasma glucose in vaccinated cows on the first week after calving (W3D1=3 days after calving). FIG. 18 demonstrates that vaccinated cows had higher plasma insulin compared to control cows. It is known that plasma glucose and insulin decrease in cows after calving. This has been interpreted as negative energy balance (NEB) and insulin resistance in postparturient dairy cows. Since plasma glucose and insulin are high in vaccinated cows compared to those of controls this suggests that translocation of endotoxin is responsible for NEB and insulin resistance observed commonly in cows after calving.

Figure 19:
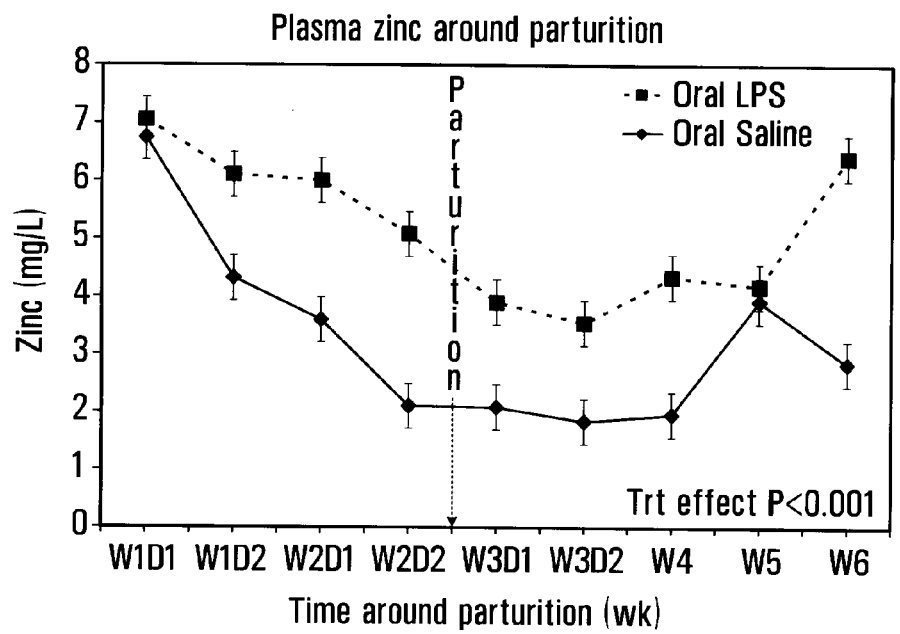
FIG. 19 is a graph depicting concentration of zinc (mg/L) in plasma of dairy cows treated with: 1) oral LPS from *E. coli* 0111:B4 (- -■- -), or 2) oral saline (-♦-), 3) intravenous LPS from *E. coli* 0111:B4 around parturition (W1D1, or 2=week 1 day 1 or day 2 of vaccination; W2D1, or 2=week 2 day 1 or day 2 of vaccination; W3D1, or 2=week 3 day 1 or day 2 of vaccination; and W4, 5, or 6=week 4, 5, or 6 of the experiment).
Figure 20:
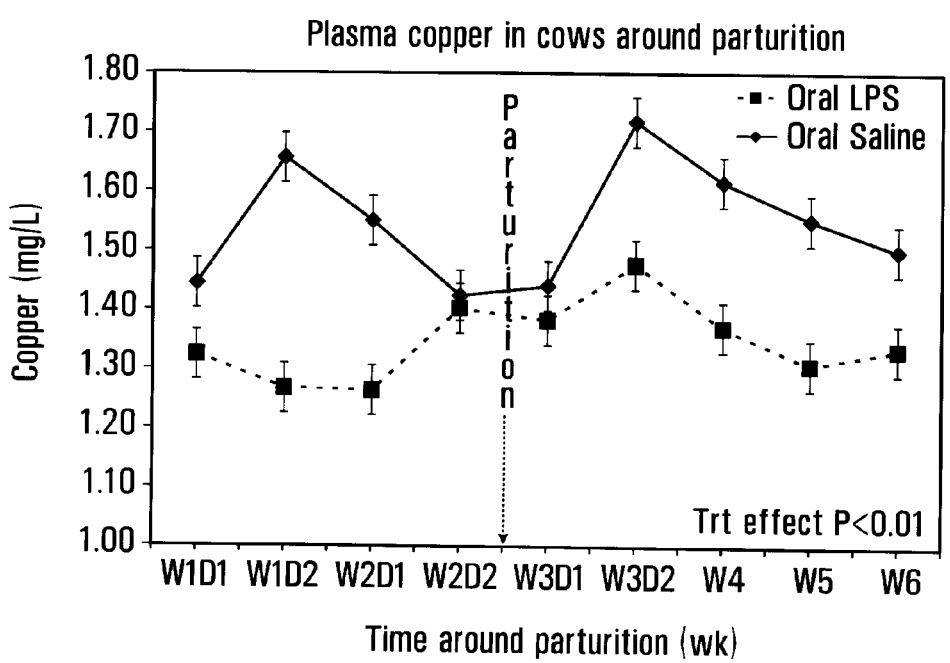
FIG. 20 is a graph depicting concentration of copper (mg/L) in plasma of dairy cows treated with: 1) oral LPS from *E. coli* 0111:B4 (- -■- -), or 2) oral saline (-♦-), 3) intravenous LPS from *E. coli* 0111:B4 around parturition (W1D1, or 2=week 1 day 1 or day 2 of vaccination; W2D1, or 2=week 2 day 1 or day 2 of vaccination; W3D1, or 2=week 3 day 1 or day 2 of vaccination; and W4, 5, or 6=week 4, 5, or 6 of the experiment).

FIGS. 19 and 20 show plasma concentrations of two main trace elements, zinc and copper, in both vaccinated and control cows. As shown in FIG. 19, plasma zinc was lower in control cows before and after parturition. It is known that plasma zinc declines during the transition period. Our data show that vaccination against bacterial LPS prevented the decline in plasma zinc around parturition. Zinc is an essential mineral for growth of bacteria. During inflammation and endotoxemia there is translocation of bacteria from gastrointestinal tract or mammary gland into the blood circulation. Usually, zinc and other minerals such as iron are sequestered by the liver so that translocated bacteria have no sources of essential minerals for their growth and multiplication. Lower plasma zinc in control cows indicates that greater amounts of endotoxin and bacteria translocated into the bloodstream of those cows. Results in FIG. 20 show that copper increased in the plasma of control cows both before and after calving. However, no changes in plasma copper occurred in vaccinated cows. Copper is increased in conditions of endotoxemia and sepsis partly because of increased Cu-binding protein ceruloplasmin. Therefore, increased copper in control cows is in agreement with the clinical finding of high incidence of metabolic and infectious disorders in those cows. Copper is important as part of many antioxidant enzymes very much needed to scavenge high amounts of oxygen radicals released during endotoxemia. Cytokines such as tumor necrosis factor-alpha, interleukin-1, and interleukin-6 appear to mediate many of the alterations seen during the acute phase response. Cytokines are released by macrophages stimulated by bacteria and endotoxin.

Figure 21:
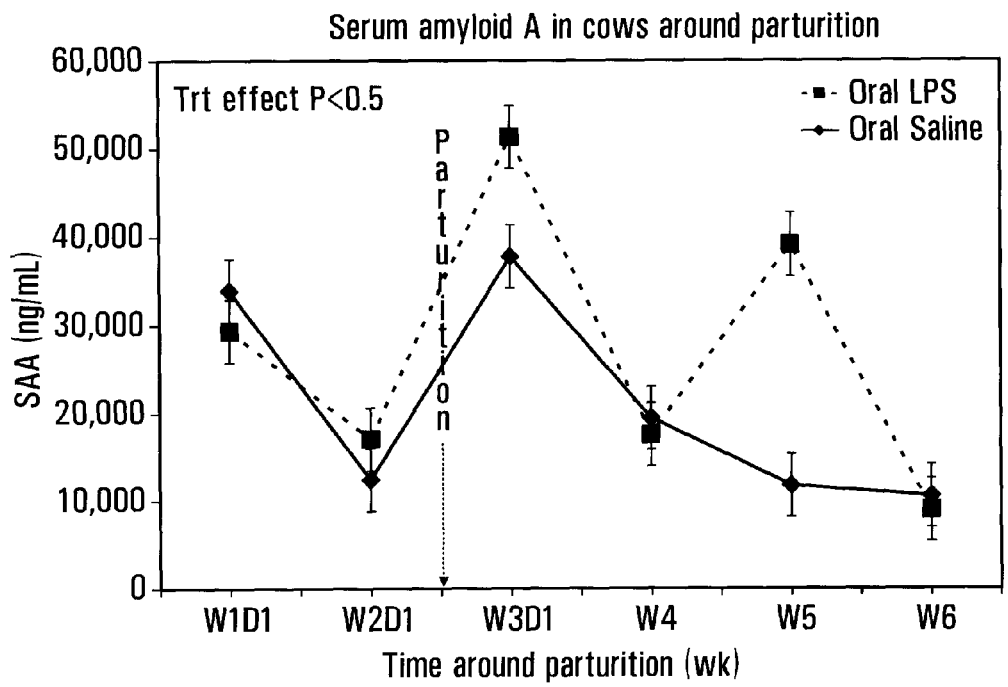
FIG. 21 is a graph depicting concentration of serum amyloid A (SAA; ng/L) in plasma of diary cows treated with: 1) oral LPS from *E. coli* 0111:B4 (- -■- -), or 2) oral saline (-♦-), around parturition (W1D1, or 2 week 1 day 1 or day 2 of vaccination; W2D1, or 2=week 2 day 1 or day 2 of vaccination; W3D1, or 2=week 3 day 1 or day 2 of vaccination; and W4, 5, or 6=week 4, 5, or 6 of the experiment).
Figure 22:
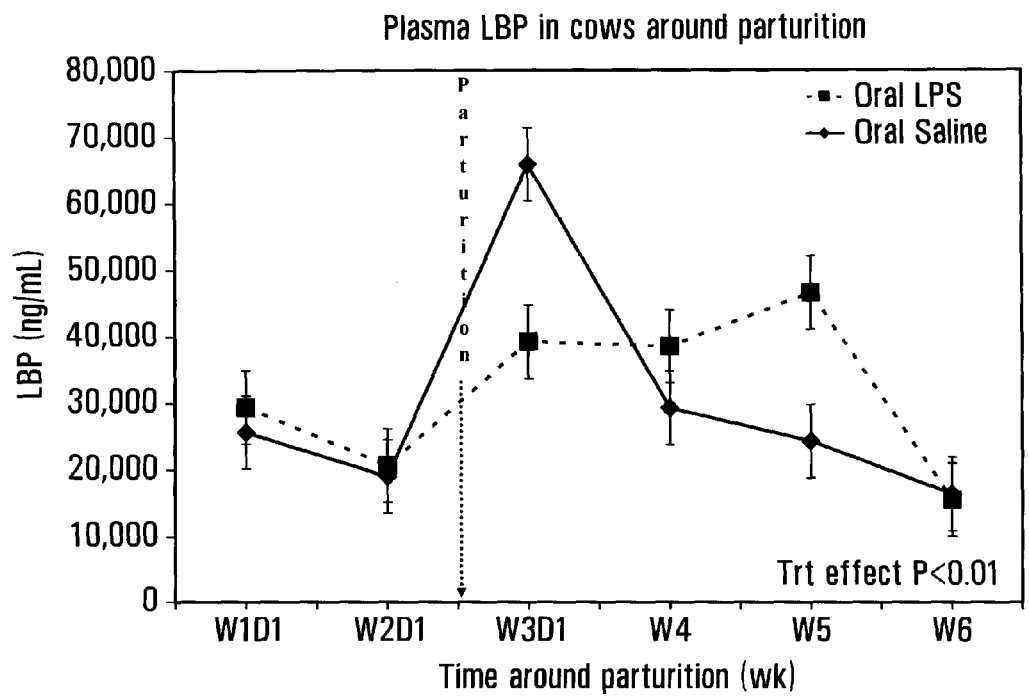
FIG. 22 is a graph depicting concentration of lipopolysaccharide-binding protein (LBP; ng/L) in plasma of dairy cows treated with: 1) oral LPS from *E. coli* 0111:B4 (- -■- -), or 2) oral saline (-♦-), 3) intravenous LPS from *E. coli* 0111:B4 around parturition (W1D1, or 2=week 1 day 1 or day 2 of vaccination; W2D1, or 2=week 2 day 1 or day 2 of vaccination; W3D1, or 2=week 3 day 1 or day 2 of vaccination; and W4, 5, or 6=week 4, 5, or 6 of the experiment).

FIGS. 21 and 22 show results for the two main plasma acute phase proteins serum amyloid A (SAA) and lipopolysaccharide-binding protein (LBP) during the experimental period. Both SAA and LBP bind and neutralize endotoxin. Although there were no significant differences in the concentration of SAA between the vaccinated and the control group, this acute phase protein increased immediately after calving in both groups of cows. These results confirm our previous reports of increased SAA during the transition period in dairy cows. The SAA is important in binding and removing endotoxin from circulation. On the other hand, plasma LBP was higher in control cows than in vaccinated ones, especially in the first 3 days after calving. Plasma LBP helps with the transferring of endotoxin to macrophages or lipoproteins and its quick removal from circulation. This again confirms higher translocation of endotoxin in control cows.

Figure 23:
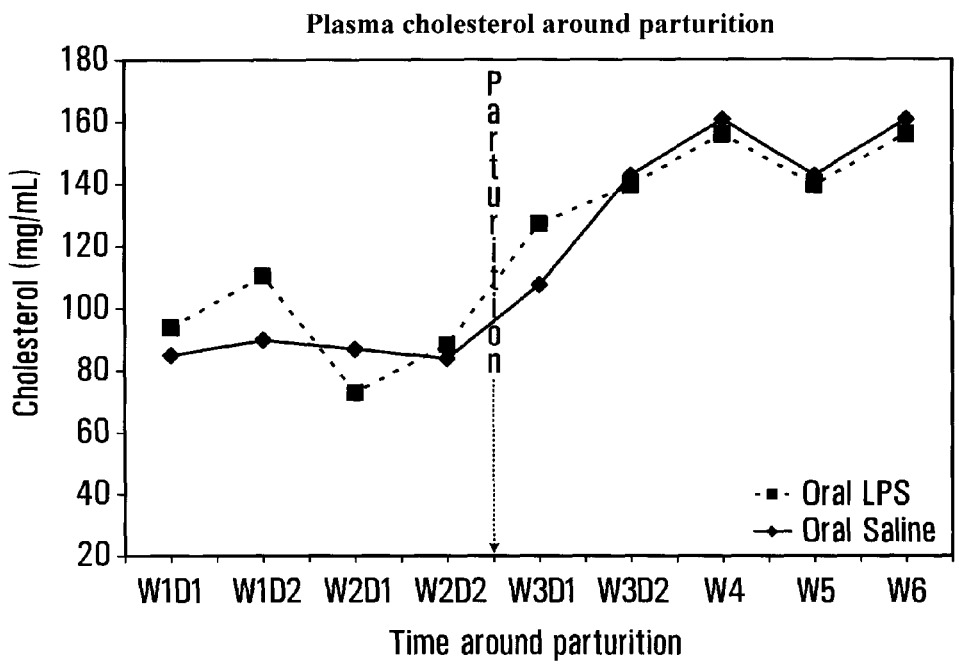
FIG. 23 is a graph depicting concentration of cholesterol (mg/ml) in plasma of diary cows treated with: 1) oral LPS from *E. coli* 0111:B4 (- -■- -), or 2) oral saline (-♦-), 3) intravenous LPS from *E. coli* 0111:B4 around parturition (W1D1, or 2=week 1 day 1 or day 2 of vaccination; W2D1, or 2=week 2 day 1 or day 2 of vaccination; W3D1, or 2=week 3 day 1 or day 2 of vaccination; and W4, 5, or 6=week 4, 5, or 6 of the experiment).
Figure 24:
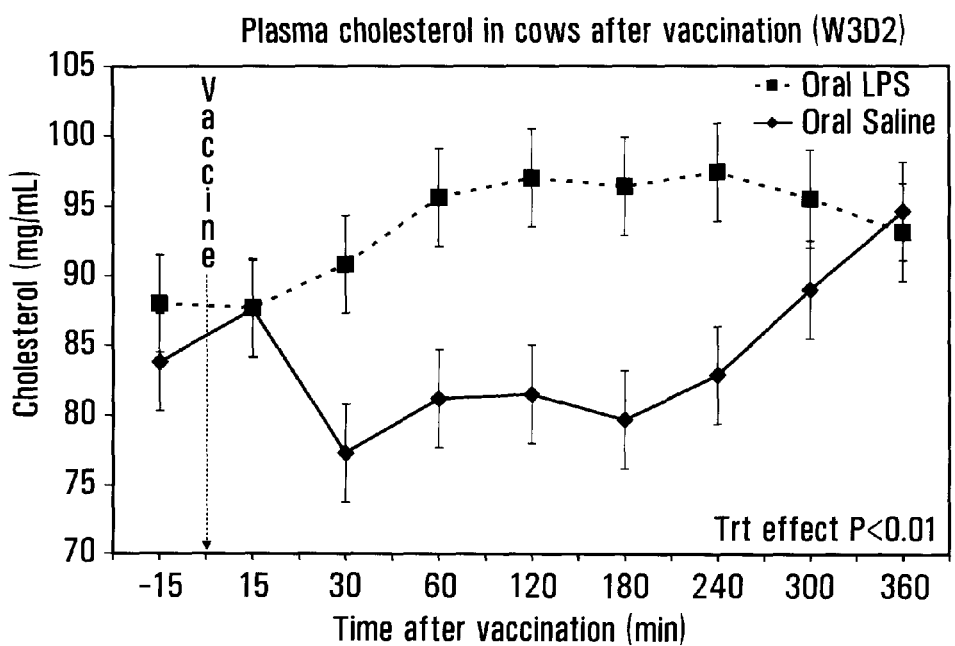
FIG. 24 is a graph depicting concentration of cholesterol (mg/mL) in the plasma of dairy cows treated with: 1) oral LPS from *E. coli* 0111:B4 (- -■- -), or 2) oral saline (-♦-) on the first wk after parturition (W3D1=week 3 day 1 of vaccination) before and after vaccination.

FIGS. 23 and 24 show plasma cholesterol in vaccinated and control cows. Plasma cholesterol did not change between the two groups during the experimental period; however, there was a different response to administration of the vaccine or saline during the last day of the vaccination. Control cows had lower cholesterol in plasma during the 6 h after treatment. Low plasma cholesterol is a common finding during conditions of endotoxemia and inflammatory disease. Indeed, control cows were affected by a variety of inflammatory (metritis and mastitis) and metabolic disorders. These data fully support clinical findings of high incidence of metabolic disorders in control cows. Higher plasma cholesterol in the vaccinated cows confirms the better health status of vaccinated cows compared to the control ones. Cholesterol is very important in bile formation. Bile plays a significant role in dispersing and deactivating endotoxin in the gastrointestinal tract. Therefore, lower plasma cholesterol suggests more cholesterol has been directed to bile formation in the control cows.

Figure 25:
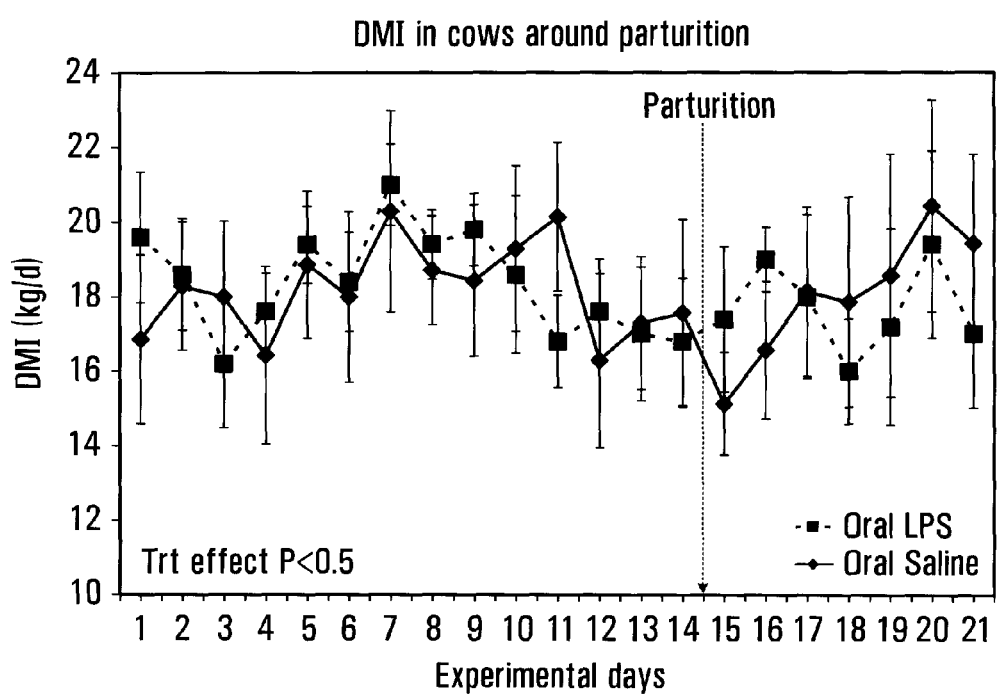
FIG. 25 is a graph depicting dry matter intake (DMI; kg/d) in dairy cows treated with: 1) oral LPS from *E. coli* 0111:B4 (--■- -), or 2) oral saline (-♦-) twice a week during 2 wk before and 1 wk after parturition (vaccination period).

FIG. 25 shows that both vaccinated and control cows had no differences in dry matter intake during the whole experimental period.

Summary of Results

The results presented indicate that:
1) Feeding dairy cows high proportions of barley grain (30 and 45% vs 0 or 15%) immediately after parturition is associated with enhanced concentrations (8- to 14-fold) of endotoxin in the ruminal fluid.
2) Presence of free endotoxin in the ruminal fluid is associated with translocation of endotoxin in the blood circulation as indicated by the in vitro study.
3) Low acidic ruminal pH and presence of endotoxin make rumen and colon tissues leaky to endotoxin and other non-nutritious compounds.
4) Translocation of endotoxin into the bloodstream is associated with activation of immune response as indicated by higher plasma SAA, LBP, and CRP in cows fed higher proportions of barley grain. These acute phase proteins are important in binding, neutralizing, and removing endotoxin from circulation.
5) Translocation of endotoxin into the bloodstream also affects many blood metabolites such as NEFA and BHBA causing fatty liver and ketosis in transition cows.
6) Prevention of endotoxin translocation is of utmost importance for prevention of metabolic disturbances during the transition period.
7) Vaccination against endotoxin (or LPS) prevented 100% metabolic disorders during the first 30 days after calving. This is the most critical period of occurrence of most of metabolic disorders in dairy cows. The vaccine also improved the occurrence of metabolic diseases by 66% after 30 days of calving.
8) Vaccination against LPS also improved immune responses (immunoglobulin production) as well as energy balance, lipid, and mineral metabolism in transition dairy cows.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Unless defined otherwise, all technical and scientific terms used herein have the same meaning as commonly understood to one of ordinary skill in the art to which this invention belongs. As used in this specification and the appended claims, the singular forms "a," "an," and "the" include plural reference unless the context clearly dictates otherwise.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for preventing occurrence after parturition of a metabolic disorder associated with grain-feeding in a grain-fed cow, said method comprising:
  (a) feeding a cow a diet comprising grain;
  (b) orally administering to said cow a composition comprising an *E. coli* lipopolysaccharide from a time no more than four weeks prior to parturition to a time no more than four weeks after parturition.

2. The method according to claim 1, wherein said metabolic disorder is associated with increased permeability of the rumen or colon.

3. The method according to claim 2, wherein said increased permeability results in translocation of bacterial endotoxin from the gastrointestinal tract to the bloodstream.

4. The method according to claim 1 wherein said metabolic disorder is ruminal acidosis, laminitis, ketosis, fatty liver, left displaced abomasum, milk fever, downer cow, retained placenta, mertritis, mastitis, udder edema or bloat.

5. The method according to claim 1, comprising administering said composition two times per week.

6. The method according to claim 1, comprising administering said composition in a dose of from 0.001 to 1 µg lipopolysaccharide/kg body weight of said cow.

7. The method according to claim 6, wherein said dose comprises from 0.01, to 0.05 µg lipopolysaccharide/kg body weight of said cow.

8. The method according to claim 6, wherein said dose comprises about 0.01, about 0.05 or about 0.1 µg lipopolysaccharide/kg body weight of said cow.

9. The method according to claim 1, wherein said lipopolysaccharide is a naturally-occurring, semi-synthetic or synthetic lipopolysaccharide.

10. The method according to claim 1, said composition being adapted for administration to the mucosal tissues.

11. The method according to claim 1, said composition being formulated as a tablet, capsule or liquid formulation.

12. The method according to claim 1, wherein the method is for preventing the metabolic disorder within the first 30 days after parturition.

13. The method according to claim 12, wherein the cow is a dairy cow.

* * * * *